(12) United States Patent
Mul et al.

(10) Patent No.: US 6,635,793 B2
(45) Date of Patent: Oct. 21, 2003

(54) PREPARATION OF EPOXIDES FROM ALKANES USING LANTHANIDE-PROMOTED SILVER CATALYSTS

(75) Inventors: Guido Mul, Nootdorp (NL); Marianna F. Asaro, Belmont, CA (US); Albert S. Hirschon, Menlo Park, CA (US); Robert B. Wilson, Jr., Palo Alto, CA (US)

(73) Assignee: SRI International, Menlo Park, CA (US)

(*) Notice: Subject to any disclaimer, the term of this patent is extended or adjusted under 35 U.S.C. 154(b) by 15 days.

(21) Appl. No.: 10/346,679

(22) Filed: Jan. 15, 2003

(65) Prior Publication Data

US 2003/0130552 A1 Jul. 10, 2003

Related U.S. Application Data

(62) Division of application No. 09/792,390, filed on Feb. 22, 2001, now Pat. No. 6,509,485.

(51) Int. Cl.⁷ .......................... C07C 5/327; C07C 5/333
(52) U.S. Cl. ................ 585/654; 585/659; 585/660; 585/661; 585/662; 585/663
(58) Field of Search ................. 585/654, 659, 585/660, 661, 662, 663

(56) References Cited

U.S. PATENT DOCUMENTS

| | | | |
|---|---|---|---|
| 3,836,481 A | 9/1974 | Kajimoto et al. | 252/462 |
| 4,010,115 A | 3/1977 | Nielsen et al. | 252/454 |
| 4,248,740 A | 2/1981 | Mitsuhata et al. | 252/463 |
| 4,342,667 A | 8/1982 | Armstrong et al. | 252/476 |
| 4,845,253 A | 7/1989 | Bowman | 549/536 |
| 5,112,795 A | 5/1992 | Minahan et al. | 502/324 |
| 5,504,053 A | 4/1996 | Chou et al. | 502/348 |
| 5,597,773 A | 1/1997 | Evans et al. | 502/348 |
| 5,618,954 A | 4/1997 | Boeck et al. | 549/534 |
| 5,625,084 A | 4/1997 | Pitchai et al. | 549/536 |
| 5,686,380 A | 11/1997 | Pitchai et al. | 502/341 |
| 5,703,254 A | 12/1997 | Gaffney et al. | 549/536 |
| 5,763,630 A | 6/1998 | Kahn et al. | 549/534 |
| 5,770,746 A | 6/1998 | Cooker et al. | 549/534 |
| 5,780,657 A | 7/1998 | Cooker et al. | 549/534 |
| 5,856,534 A | 1/1999 | Cooker et al. | 549/534 |
| 5,861,519 A | 1/1999 | Kahn et al. | 549/536 |
| 5,864,047 A | 1/1999 | Gaffney | 549/536 |
| 5,939,569 A | 8/1999 | Jones et al. | 549/512 |
| 5,973,171 A | 10/1999 | Cochran et al. | 549/533 |
| 6,392,066 B1 | 5/2002 | Mul et al. | 549/534 |

FOREIGN PATENT DOCUMENTS

| | | |
|---|---|---|
| CA | 1282772 | 4/1991 |
| JP | 50112292 | 9/1975 |

OTHER PUBLICATIONS

Bettahar et al. (1996), "On the Partial Oxidation of Propane and Propylene on Mixed Metal Oxide Catalysts," *Applied Catalysis A: General* 145:1–48.

Breitscheidel et al. (1991), "Metal Complexes in Inorganic Matrices. 7.[1] Nanometer–Sized, Uniform Metal Particles in a $SiO_2$ Matrix by Sol–Gel Processing of Metal Complexes," *Chem. Mater.* 3(3):559–566.

Carrazàn et al. (1997), "Promotion of Selectivity to Propene in $Mg_3V_2O_8$ Catalysts by Oxygen Spillover in the Oxidative Dehydrogenation of Propane," *ACS Symposium Series* 638:223–235.

Chaar et al. (1988), "Selective Oxidative Dehydrogenation of Propane Over V–Mg–O Catalysts," *Journal of Catalysis* 109:463–467.

Geenen et al. (1982), "A Study of the Vapor–Phase Epoxidation of Propylene and Ethylene on Silver and Silver–Gold Alloy Catalysts," *Journal of Catalysis* 77:499–510.

Giordano et al. (1981), "Epoxidation of Ethylene on Silver–Loaded Zeolites," *Zeitschrift für Physikalische Chemie Neue Folge, Bd.* 127:109–124.

Hoang et al. (1997), "Surface Chemistry of Supported Chromium Oxide on Lanthanum Carbonate," *Journal of Catalysis* 171:313–319.

Jacobs et al. (1979), "Some Unusual Properties of Activated and Reduced AgNaA Zeolites," *Journal of the Chemical Society* 1:56–64.

Ji et al. (1996), "The Oxidative Dehydrogenation of Ethane Over Alkali–Doped Lanthanum–Calcium Oxide Catalysts," *Catalysis Letters* 39:247–252.

Kim et al. (1991), "Selective Oxidation of Propane Involving Homogeneous and Heterogeneous Steps Over Multicomponent Metal Oxide Catalysts," *Applied Catalysis* 70:175–187.

Sachtler et al. (1981), "On the Mechanism of Ethylene Epoxidation," *Catalysis Reviews, Science and Engineering* 23 (1&2):127–149.

Sam et al. (1990), "Oxidative Dehydrogenation of Propane Over V–Mg–O Catalysts," *Journal of Catalysis* 123:417–435.

Savary et al. (1997), "Characterization of $AgMo_3P_2O_{14}$ Catalyst Active in Propane Mild Oxidation," *Journal of Catalysis* 169:287–300.

Stern et al. (1997), "Oxydehydrogenation of N–Butane Over Promoted Mg–V–Oxide Based Catalysts," *Applied Catalysis A: General* 153:21–30.

Toreis et al. (1987), "The Oxidation of Ethylene Over Silver–Based Alloy Catalysts," *Journal of Catalysis* 108:161–174.

Wang et al. (1995), "The Effect of Chloride Ions on a $Li^+$–MgO Catalyst for the Oxidative Dehydrogenation of Ethane," *Journal of Catalysis* 151: 155–167.

*Primary Examiner*—Ba K. Trinh
(74) *Attorney, Agent, or Firm*—Reed & Eberle LLP

(57) ABSTRACT

A process is provided for use in the conversion of alkanes into alkylene oxides, having particular utility in the conversion of propane to form propylene oxide, using a lanthanide-promoted, supported, silver catalyst prepared via precipitation. A preferred embodiment uses silver nitrate and lanthanum nitrate to form the catalyst on a $BaCO_3$ support.

17 Claims, 1 Drawing Sheet

PREPARATION OF EPOXIDES FROM ALKANES USING LANTHANIDE-PROMOTED SILVER CATALYSTS

CROSS REFERENCE TO RELATED APPLICATIONS

This application is a divisional of U.S. Ser. No. 09/792,390, filed on Feb. 22, 2001 now U.S. Pat. No. 6,509,485B2.

TECHNICAL FIELD

This invention relates generally to novel catalysts for use in the direct epoxidation of alkanes to form alkylene oxides, having particular utility in the conversion of propane to propylene oxide. The catalyst is prepared via precipitation and is a lanthanide-promoted, supported silver catalyst. The invention also relates to methods for catalyzing oxidative chlorination/halodehydrogenation and epoxidation reactions using the novel catalyst, and to methods for manufacturing the novel catalysts. The invention finds utility in the fields of catalysis.

BACKGROUND

Conversion of alkanes to oxygenates is typically considered to proceed via oxidative dehydrogenation of an alkane to an alkene followed by epoxidation of the alkene to provide an oxide in a separate process. A direct method of synthesizing alkylene oxides from an alkane such as propane has not been practical heretofore as activation of the propane requires high temperatures, which decompose partial oxidation products, particularly propylene oxide, or promote total oxidation.

Numerous studies have been conducted investigating the oxidative dehydrogenation of alkanes to produce alkenes. See, for example, Chaar et al. (1988) *J. Catal.* 109: 463, Siew Hew Sam et al. (1990) *J. Catal.* 123:417, and Stern et al. (1997) *Appl. Catal. A: General,* 153:21. Various magnesium vanadates are reported to yield propylene with particularly high selectivity and, when a second oxidic phase ($Sb_2O_4$) is added, selectivities of up to 95% have been achieved. Carrazan et al. (1997) *ACS Symp. Ser.* 638:223. The mechanisms by which the oxidative dehydrogenation occurs and the interactions responsible for high selectivity are yet to be identified.

Other than vanadium-based catalysts, several molybdenum and niobium catalysts have also been investigated for use in oxidative dehydrogenation. See, for example, Breitescheidel et al. (1991) *Chem. Mater.* 3:559, Geenen et al. (1982) *J. Catal.* 77:499 and Toreis et al. (1987) *J. Catal.* 108:161. Bettahar et al. (1996) *Appl. Catal. A: General* 145:1 and Kim et al. (1991) *Appl. Catal.* 70:175 discloses that molybdates of, for example, nickel or cobalt, yield acrolein in substantial amounts, thereby decreasing the selectivity toward propylene. Niobium oxide, particularly in combination with vanadium or molybdenum, has been shown to have high selectivity for propylene in the oxidative dehydrogenation of propane in Savary et al. (1997) *J. Catal.* 169:287.

Catalyst compositions without molybdenum or vanadium have also been known to perform oxidative dehydrogenation. Ji et al. (1996) *Catal. Lett.* 39:247 and Wang et al. (1995) *J. Catal.* 151:155 discuss the selectivity of combinations of lanthanum oxide, alkaline earth metal, and alkali metal. Unfortunately, temperatures in excess of 400° C. are required for any of the above-mentioned catalysts to have significant activity and such temperatures result in decomposition of the propylene oxide.

Catalysts composed of lanthanum carbonate and chromium oxide have been shown to be active and selective at lower temperatures but have only been used in the oxidative dehydrogenation of isobutane, see Hoang et al. (1997) *J. Catal.* 171:313. Carbonate-supported catalysts are currently used in ethylene epoxidation and often contain reduced silver and an alumina carrier. Catalysts of this nature have been described in U.S. Pat. No. 4,248,740 to Mitsuhata et al. and U.S. Pat. No. 4,342,667 to Armstrong et al.

It has now been unexpectedly discovered that a highly selective catalyst capable of "one-pot" conversion of an alkane to an alkylene oxide can be obtained by using an alkaline earth metal carbonate as a support in combination with a rare earth metal promoter. Also surprising is the finding that such catalysts are capable of the selective oxidative dehydrogenation of alkanes at temperatures under 400° C.

SUMMARY OF THE INVENTION

Accordingly, it is a primary object of the invention to provide a process for the conversion of an alkane to an alkylene oxide at temperatures less than 400° C.

Additional objects, advantages and novel features of the invention will be set forth in part in the description which follows, and in part will become apparent to those skilled in the art upon examination of the following, or may be learned by practice of the invention.

In a first embodiment, a novel process for the conversion of alkane to alkylene oxide is provided wherein an alkane and oxygen-containing gas feedstream contacts an alkaline earth metal carbonate-supported silver catalyst comprised of a catalytically effective amount of silver, and a promoting amount of a lanthanide metal promoter, an alkali metal halide, an alkali metal nitrate, and an optional transition metal promoter.

In another embodiment of the invention, a novel process for the conversion of propane to propylene oxide is provided wherein a propane and oxygen-containing gas feedstream contacts an alkaline earth metal carbonate-supported silver catalyst that has a catalytically effective amount of silver, and a promoting amount of a lanthanide metal promoter, an alkali metal halide, an alkali metal nitrate, and an optional transition metal promoter.

In a further embodiment of the invention, a novel catalyst composition is provided comprising an alkaline earth metal carbonate support, a catalytically effective amount of silver, an effective promoting amount of a lanthanide metal promoter, an effective promoting amount of an alkali metal halide, an effective promoting amount an alkali metal nitrate, and a promoting amount of a transition metal promoter.

In yet another embodiment of the invention, a novel process for the conversion of alkane to alkene is provided comprising contacting, at a temperature in the range of approximately 200° C. to 400° C., a feedstream, comprised of alkane and an oxygen-containing gas, and a supported silver catalyst, comprised of an inert refractory solid support comprised of alkaline earth metal carbonate, a catalytically effective amount of silver, an effective promoting amount of a halide anion, an effective promoting amount of a rare earth metal promoter, an effective promoting amount of a sodium promoter, and an optional effective promoting amount of a transition metal promoter.

In still another embodiment of the invention, a novel process for the conversion of propane to propylene is provided comprising contacting, at a temperature in the range of approximately 200° C. to 400° C., a feedstream, comprised of propane and an oxygen-containing gas, and a supported silver catalyst comprised of an inert refractory solid support comprised of alkaline earth metal carbonate, a catalytically effective amount of silver, an effective promoting amount of a halide anion, an effective promoting amount of a rare earth metal promoter, an effective promoting amount of a sodium promoter, and an optional effective promoting amount of a transition metal promoter.

DETAILED DESCRIPTION OF THE INVENTION

Definitions and Nomenclature

Figure 1:
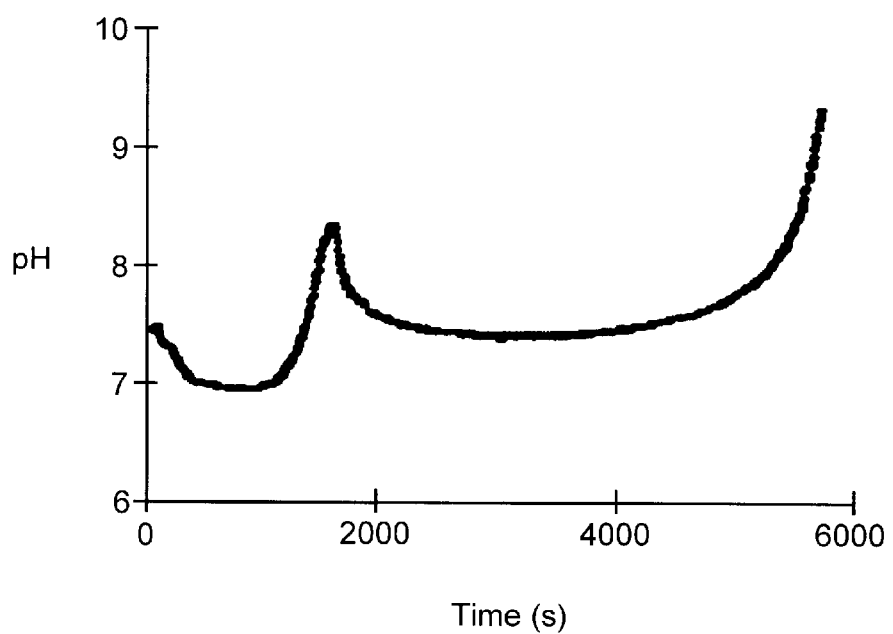
FIG. 1 presents a precipitation curve obtained during catalyst synthesis, as described in Example 17.

Before the present compounds, compositions, and methods are disclosed and described, it is to be understood that, unless otherwise indicated, this invention is not limited to specific support structures, reagents, methods of preparation, or the like, as such may vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. Thus, for example, reference to "a promoter" includes one or more promoters; reference to "a support" includes one or more supports, and the like.

The term "alkali metal" refers to elements of Group 1 of the Periodic Table, i.e., lithium, sodium, potassium, rubidium, cesium, and francium.

The term "alkali earth metal" refers to elements of Group 2 of the Periodic Table, i.e., beryllium, magnesium, calcium, strontium, barium, and radium.

The term "rare earth metal" refers to elements of the lanthanide and actinide series of the Periodic Table.

For the purposes of this invention, the term "conversion" is taken to mean the mole percent of propylene lost from the feed stream as a result of reaction. Likewise, the phrase "selectivity to propylene oxide" is taken to mean the mole percent of reacted propylene that is used to form propylene oxide. The conversion and selectivity of the process of this invention can vary over a wide range. Process variables influencing conversion and selectivity include temperature, flow rate, concentration of oxygen, and concentration of propylene. Generally, as the concentration of propylene in the feed stream decreases, the conversion of propylene and the selectivity for propylene oxide decrease as well.

A "support" is a carrier that comprises the catalytically active components of a supported, i.e., heterogeneous, catalyst. In the present catalyst, the support is comprised of an alkali earth metal carbonate.

A "promoter" means a component that provides an improvement in one or more of the catalytic properties of the catalyst, e.g., selectivity, activity, conversion, stability, and yield, as compared to a catalyst not containing the promoter. "Effective promoting amount" means an amount of a promoter sufficient to yield the above-mentioned improvement.

"Halo" or "halogen" refers to fluoro, chloro, bromo, or iodo, and usually relates to halide substitution for a hydrogen atom in an organic compound. Of the halides, chloro and fluoro are generally preferred.

"Optional" or "optionally" means that the subsequently described event or circumstance may or may not occur, and that the description includes instances where said event or circumstance occurs and instances where it does not. For example, the phrase "catalyst containing an optional transition metal anion" means that a transition metal anion may or may not be present and that the description includes catalysts that comprise a transition metal anion and catalysts that do not.

The phrase "redox half-reaction" as used herein refers to half-reactions such as those found in equations presented in tables of standard reduction or oxidation potentials, also known as standard or single electrode potentials, of the type found in, for instance, the Handbook of Chemistry and Physics, CRC Press, 1995, pages D155–162.

As used herein, all references to the Periodic Table of the Elements and groups thereof is to the version of the table published by the Handbook of Chemistry and Physics, CRC Press, 1995, which uses the IUPAC system for naming groups.

The Novel Process

The primary embodiment of the invention relates to a method of converting alkane into alkylene oxide using alkali earth metal carbonate supported catalysts. Such catalysts are fully described below and in U.S. Pat. No. 6,392,066, entitled "Epoxidation of Olefins Using Lanthanide-Promoted Silver Catalysts". The method comprises contacting an alkane with oxygen in the presence of the catalyst composition under conditions such that alkylene oxide is formed. The method of the invention is of significant utility in the conversion of propane to propylene oxide but also is suitable for use with other alkanes including, but not limited to, ethane, butane, pentane, and the like.

While not wishing to be limited to a single theory, it is believed that the conversion of an alkane to alkylene oxide proceeds via initial oxidative chlorination of the alkane, followed by conversion of the chlorinated intermediates to alkene and subsequent epoxidation of the alkene to form an alkylene oxide. Evidence supporting the theory that oxidative chlorination is the initial reaction pathway is found by substituting chlorinated species for alkane in the feed stream and observation of alkene and alkylene oxide in the product stream. In propane-based applications, both 1- and 2-chloropropane are such intermediates and, under certain circumstances, may be observed in the product stream.

The oxygen employed in the aforementioned process may be obtained from any gas containing molecular oxygen, such as air, commercially pure oxygen, or other substance that, under the conditions necessary for oxidative dehydrogenation, both exists in a gaseous state and forms molecular oxygen. The alkane and oxygen are present as an alkane and oxygen-containing gas feedstream in amounts sufficient to allow formation of the alkylene oxide. The concentration of alkane, such as ethane or propane, in the feedstream is preferably in the range of about 0.1% to about 25%, with concentrations ranging from about 1% to about 20% being preferred and concentrations ranging from about 2% to about 55% being most preferred. Similarly, the concentration of oxygen in the feedstream is in the range of about 0.1% to about 25%, with concentrations ranging from about 1% to about 20% being preferred and concentrations ranging from about 2% to about 15% being most preferred.

The feedstream may also contain, but preferably does not contain, a gaseous efficiency-enhancing member of a redox-half reaction and/or a gas phase halogen compound, such as an alkyl halide. The gaseous efficiency-enhancing materials are compounds containing an element capable of existing in more than two valence states, preferably nitrogen, and another element that is preferably oxygen. Examples of gaseous efficiency-enhancing members of a redox-half reaction pair include, but are not limited to, at least one of NO, $NO_2$, $N_2O_4$, $N_2O_3$, or any gaseous substance capable of forming one of the aforementioned gases, particularly NO and $NO_2$, under dehydrogenation conditions. NO is most preferred. The gaseous efficiency-enhancing member of a redox-half reaction is typically not present and is not necessary for conversion of the alkane into an alkylene oxide. If present in the feedstream, however, the gaseous efficiency-enhancing member is present in concentrations ranging from about 0.1 ppm to about 2,000 ppm. Concentrations ranging from about 1 ppm to about 1000 ppm are preferred and concentrations ranging from about 50 ppm to about 500 ppm are most preferred.

Gas phase halogen compounds are preferably not included in the feedstream. If included, however, such a gas phase halogen compound is preferably an organic halide, saturated or unsaturated, such as 1-chloropropane, 2-chloropropane, ethylene dichloride, ethyl chloride, vinyl chloride, methyl chloride and methylene chloride. Ethyl chloride, 1-chloropropane, and 2-chloropropane are preferred. If used, the gas phase halogen compound is generally present in concentrations ranging from about 0.1 ppm to about 2,000 ppm. Concentrations ranging from about 1 ppm to about 1000 ppm are preferred and concentrations ranging from about 50 ppm to about 100 ppm are most suitable.

The remainder of the feedstream may be made up of an inert gas such as argon, nitrogen or helium as a ballast or diluent. Varying amounts of carbon dioxide and water vapor may also be present, depending upon whether means have been provided to remove such substances from the feedstream components. It is preferred that no carbon dioxide be present in the feedstream as the inclusion of carbon dioxide results in lower selectivity.

The reactants can be contacted with the catalyst in any suitable reactor. Preferred are tubular stainless steel reactors designed to withstand the pressure and temperature of the reaction. While the reaction can take place in either the gaseous phase or in a liquid solvent, contact in the gaseous phase is preferred. The oxygen/alkane feed stream is preferably preheated to a temperature approximately that of the reaction temperature. The reaction can be conducted at any operable temperature upon contacting the catalyst and the reactants. Generally, suitable reaction temperatures are above 50° C. and preferred temperatures are in the range of about 200° C. to about 400° C., with temperatures in the range of about 250° C. to about 350° C. most preferred. The pressure and temperature should be adjusted to achieve optimal results for the particular catalyst and feedstream being used. Generally, pressures range from about 1 atmosphere to about 30 atmospheres with atmospheric pressure being preferred.

The duration of time the reactants must remain in contact with the catalyst must be sufficient to allow for oxidative chlorination of the alkane, halodehydrogenation of the chlorinated product, and epoxidation of the alkene intermediate produced by the halodehydrogenation. Generally, the duration of the contact varies according to the size of the reactor and the amount of catalyst used. Contact time is controlled by variation of the gas hourly space velocity of the feedstream as it passes through the reactor. Typically, space velocities in the range of from about 10 $hr^{-1}$ to about 15,000 $hr^{-1}$ are suitable. Space velocities in the range of from about 100 $hr^{-1}$ to about 6,000 $hr^{-1}$ are preferred and space velocities in the range of from about 500 $hr^{-1}$ to about 3,000 $hr^{-1}$ are most preferred.

If propane is used in the feedstream, the propylene oxide reaction product is a useful industrial intermediate, particularly in the manufacture of urethane polymers. Propylene oxide is also useful in the production of propylene glycol, which is used to form plastics, and in the production of propene glycol ethers, which are used as solvents. The alkene reaction product from other alkane feedstocks can be used to generate other alkylene oxides, and any haloalkyl by-products can be used to regenerate the catalyst, as will be appreciated by those skilled in the art.

Typically, the catalyst of this invention produces an alkane conversion of at least about 1 percent. Preferably, the catalyst produces a conversion greater than about 5 percent, more preferably a conversion greater than about 8 percent, and most preferably, greater than about 10 percent. Also, the catalyst of this invention produces a selectivity to alkylene oxide greater than about 1 percent, preferably greater than about 2 percent, and more preferably greater than about 5 percent. Selectivity for alkenes ranges from about 10% to about 40%.

The Catalyst

The catalysts of the invention are alkaline earth metal carbonate supported, silver catalysts that incorporate a promoting amount of a rare earth metal promoter, a halide promoter, an alkali metal, and an alkali metal nitrate. The alkaline earth metal carbonate may be any carbonate of any element of Group 2. Suitable carbonates are described, for example, in Canadian Patent No. 1,282,772 to Thorsteinson and include, but are not limited to, calcium carbonate, barium carbonate, strontium carbonate and magnesium carbonate. Calcium and barium carbonates are preferred. The alkaline earth metal carbonate may constitute from about 40% w/w to about 60% w/w of the catalyst composition. Preferably, the alkaline earth metal carbonate is present in the range of about 45% w/w to about 55% w/w of the catalyst composition.

The silver is generally, although not necessarily, in the form of silver carbonate and is present in the range of about 20% w/w to about 50% w/w. Preferably, the silver is present in the range of about 25% w/w to about 45% w/w of the catalyst.

The rare earth metal promoter can be selected from any of the elements of the lanthanide series, i.e., atomic number 57 to atomic number 70. Suitable promoters include, but are not limited to, lanthanum, cerium, praseodynium, gadolinium and erbium. Lanthanum is preferred. The rare earth metal promoter is present in amounts in the range of about 0.1% w/w to about 20% w/w of the catalyst composition. The rare earth metal promoter is preferably present in amounts in the range of 1% w/w to about 15% w/w and most preferably present in amounts in the range of about 5% w/w to about 10% w/w of the catalyst.

The catalyst is also infused with an alkali metal nitrate in addition to the alkali metal nitrates formed by the recombination of the nitrate and alkali salts used during the synthesis of the catalyst, as will be discussed below. The metal anion in the alkali metal nitrate may be selected from any of the elements of Group 1. Preferred alkali metal anions include sodium and potassium, with sodium most preferred. The alkali metal nitrate is generally present in an amount sufficient to achieve an amount of alkali in the final catalyst in the range of between about 0.1% w/w to about 2% w/w, preferably between about 0.3% w/w and 0.7% w/w, and most preferably about 0.5% w/w.

Alkali metal halide promoters are also present in the catalyst. Such promoters may be added to the catalyst composition in the form an alkali metal halide or other soluble halide compound, i.e., HCl. Suitable alkali metal halide promoters include, for example, sodium chloride, sodium bromide, potassium chloride and potassium bromide. Preferred alkali metal halides are sodium chloride and sodium bromide, with sodium chloride most preferred. The halide promoter may be present in an amount ranging from about 0.005 to about 0.05 g Cl/g Ag, preferably from about 0.01 g Cl/g Ag to about 0.02 g Cl/g Ag. In terms of molar ratios, this represents an Cl/Ag molar ratio of about 0.015 mol Cl/mol Ag to about 0.15 mol Cl/mol Ag, preferably between about 0.03 mol Cl/mol Ag to about 0.06 mole Cl/mole Ag.

Optionally, the catalyst may be infused with a transition metal anion in the form of a carbonate or nitrate in addition to the alkali metal carbonates and nitrates formed by the recombination of the carbonate, nitrate and alkali salts used during the synthesis of the catalyst, as will be discussed below. The transition metal anion may be selected from any of the elements of Groups 3, 4, 5, 6, 7, and 8. Preferred transition metal anions include chromium, magnesium, and copper. When included, the transition metal anion is present in an amount sufficient to achieve an amount of transition metal in the catalyst in the range of between about 0.1% w/w to about 15% w/w, preferably between about 1% w/w and 10% w/w.

The catalyst composition may also contain an additional support element. Suitable supports include, but are not limited to, alumina, silica, titania, alkaline earth metal oxides, rare earth oxides, and mixtures of the above. Preferred catalysts do not contain additional support elements.

The catalyst compositions may be formed using standard precipitation methods. Such precipitation methods are well known in the art, see, for example, U.S. Pat. No. 5,625,084 to Pitachai et al., U.S. Pat. No. 3,3836,481 to Kajimoto et al., and U.S. Pat. No. 5,618,954 to Boeck et al. A basic solution containing an alkali metal carbonate and an alkali metal hydroxide is reacted with an aqueous precursor solution containing a suitable alkaline earth metal salt, a silver salt, a rare earth metal promoter, an alkali metal nitrate and an alkali metal halide promoter and, optionally, a transition metal carbonate as discussed above. The precursor solution may be acidified using nitric acid. Acidification of the precursor solution assists in the dissolution of the precursor salts and the solution may be acidified to a pH of about 3. Such acidification generally takes place prior to the addition of the basic solution. It should be noted that although other acids, such as HCl, may be used to acidify the solution, sulfuric acid or phosphoric acid are not favored as these acids may result in the formation of sulfates and phosphates which are not desired in the final catalyst. Organic acids are also disfavored. If HCl is used to acidify the precursor solution, it may only be added in limited amounts as the total concentration of halide in the catalyst should be in an amount ranging from about 0.005 g Cl/g Ag to about 0.05 g Cl/g Ag, preferably from about 0.01 g Cl/g Ag to about 0.02 g Cl/g Ag, as discussed above.

In one precipitation method, method A, the basic solution is injected by pump into the precursor solution to form a precipitation solution. The pH of the precipitation solution is monitored and the injection of the basic solution is terminated when the pH of the precipitation solution indicates that all silver and alkaline earth metals have precipitated out, generally at a pH of about 10. In a second precipitation method, method B, the basic solution and the precursor solution are simultaneously added to a separate water-containing precipitation vessel forming the precipitation solution therein. The pH of the precipitation solution is monitored and the injection rate of the basic solution is controlled to maintain the pH of the precipitation solution at a desired level, generally in the range of about pH 10 to about pH 12. The rate of precursor injection is held constant, in the range of about 10 mL/h to about 1000 mL/h.

During precipitation, the carbonate ion from the alkali metal carbonate interacts with the alkaline earth metal ion and the silver ion contained in the precursor solution, forming the silver-containing alkaline earth metal carbonate support, which then precipitates out of solution. Similarly, the alkali metal ion from the basic solution and the nitrate and carbonate ions from the precursor and basic solutions interact to form alkali metal nitrates and carbonates. Formation of alkali carbonates from these substituents will be most favored. Promoting amounts of the rare earth metal promoter and alkali metal nitrate and alkali metal halide promoters, if included, are also contained in the resulting precipitate.

When method A is used, the components of the catalyst precipitate sequentially. It is observed that the rare earth metal promoter and the silver co-precipitate out of the solution first, as hydroxides, hydroxycarbonates, and/or carbonates, at a pH of about 7. This is followed by the alkaline earth metal carbonate, which precipitates from about pH 7.5 to about pH 8.5. When method B is used, the various components co-precipitate out of solution.

The resulting precipitate is then filtered, dried and calcined at sufficient temperature and for a sufficient time to reduce the silver precursor without decomposing the alkali nitrates or alkali halogen promoters, generally at about 300° C. to about 350° C. for 10 to 20 minutes or less. It is important to note that the precipitate is not washed before drying and calcination in order to maintain the level of alkali present. The activity of the catalyst may be tested using a quartz flow reactor attached to an automatic sampling valve for GC analysis.

The alkali metal carbonate used in the basic solution may be any selected from potassium carbonate, sodium carbonate, rubidium carbonate, or cesium carbonate, or mixtures thereof. Potassium carbonate and sodium carbonate are preferred and sodium carbonate is most preferred.

The alkali metal hydroxide is used to control the pH of the precipitation solution and to provide additional alkali ions. Suitable alkali hydroxides are sodium hydroxide and potassium hydroxide. Sodium hydroxide is preferred.

The alkaline earth metal salt may be any salt that will not adversely react with the other components utilized. Suitable salts include, but are not limited to, nitrates, nitrites, propionates, sulfates, chlorates, perchlorates and chlorites. Examples of specific alkaline earth metal salts include, but are not limited to, calcium nitrate, barium nitrate, magnesium nitrate, strontium nitrate, calcium sulfate, barium sulfate, magnesium sulfate, strontium sulfate. Barium nitrate and calcium nitrate are preferred and barium nitrate is most preferred.

The silver salt may be any salt that will not adversely react with the other components utilized. Suitable salts include, but are not limited to, nitrates, nitrites, propionates, sulfates, chlorates, perchlorates and chlorites. Examples of specific silver salts include, but are not limited to, silver nitrate, silver sulfate, silver chlorate, silver sulfate, silver nitrite, silver propionate, silver perchlorate, silver chlorite and mixtures thereof. Silver nitrate is preferred.

The transition metal anion used in the precursor solution may be selected from chromium hydroxy carbonate, $Cu(NO_3)_2$, $Mg(NO_3)_2$, or mixtures thereof. Chromium hydroxy carbonate and $Mg(NO_3)_2$ are most preferred

Experimental

It is to be understood that, while the invention has been described in conjunction with the preferred specific embodiments thereof, the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLE 1

Preparation of Catalyst

A catalyst of the invention was alternatively prepared according to the following procedure. A basic solution containing 1 g NaOH and 15 g of $K_2CO_3$ in 200 mL of purified water was prepared. A precursor solution having a pH of 4.0 was prepared by first dissolving 3.5 g $Ba(OH)_2$ in $HNO_3$ and then dissolving 1 g $La(NO_3)_2.6H_2O$, 30 mg NaCl, 5 g $NaNO_3$, and 2.5 g $AgNO_3$. The basic solution was then injected into the precursor solution using a Gilson peristaltic pump at a rate of 50 mL/h with vigorous stirring. A brownish precipitate formed. The precipitation was complete in 50 minutes and injection of the basic solution was stopped at a final pH of 10. The precipitated catalyst was filtered and dried at 160° C. for 30 minutes. The catalyst was then calcined in flowing air at 325° C. for 15 minutes.

EXAMPLE 2

Alternative Preparation of Catalyst

A catalyst of the invention was alternatively prepared according to the method of Example 1. A basic solution containing 1 g NaOH and 11.5 g of $Na_2CO_3$ in 200 mL of purified water was prepared. A precursor solution having a pH of 4.0 was prepared by first dissolving 3.5 g $Ba(OH)_2$ in $HNO_3$ and then dissolving 1 g $La(NO_3)_2.5H_2O$, 1.5 g $Cr(NO_3)_2$. 9 $H_2O$, 50 mg, NaCl, 5 g $NaNO_3$, and 2.5 g $AgNO_3$. The basic solution was then injected into the precursor solution using a Gilson peristaltic pump at a rate of 50 mL/h with vigorous stirring. A dark blue precipitate formed. The precipitation was complete in 50 minutes and injection of the basic solution was stopped at a final pH of 10. The precipitated catalyst was filtered and dried at 160° C. for 30 minutes. The catalyst was then calcined in flowing air at 300° C. for 30 minutes. A bright yellow catalyst resulted.

EXAMPLE 3

Alternative Catalyst Preparation

A catalyst of the invention was alternatively prepared according to the method of Example 1. A basic solution containing 1 g NaOH and 11.5 g of $Na_2CO_3$ in 200 mL of purified water was prepared. A precursor solution having a pH of 4.0 was prepared by first dissolving 3.5 g $Ba(OH)_2$ in $HNO_3$ and then dissolving 1 g $La(NO_3)_2.5H_2O$, 1.5 g $Mg(NO_3)_2.H_2O$, 50 mg NaCl, and 2.5 g $AgNO_3$. The basic solution was then injected into the precursor solution using a Gilson peristaltic pump at a rate of 50 mL/h with vigorous stirring. The precipitation was complete in 50 minutes and injection of the basic solution was stopped at a final pH of 10. The precipitated catalyst was filtered and dried at 160° C. for 30 minutes. The catalyst was then calcined in flowing air at 300° C. for 30 minutes.

EXAMPLE 4

Activity Testing

The activity of all of the catalysts of Examples 1–3 was tested according to the following method. 2.5 g of 20 to 48 mesh catalyst was placed in a quartz flow reactor, with a flow of 40 mL/min of 5% propane, 5% $O_2$, and balance He, at atmospheric pressure. Space velocity was 1200 $h^{-1}$. The hydrocarbon/oxygen gas mixture composition was controlled using electronic mass flow controllers. The effluent from the reactor was led through a heated transfer line into an automating sampling valve for GC analysis. The GC includes column switching between a 1-foot HP 13×molecular sieve column and an Alltech Hayesep D 100/12 column, to optimize the separation of both fixed gases and higher hydrocarbons. A flame ionization detector (FID) was place in series with a thermal conductivity detector (TCD) to provide better quantification of hydrocarbons, especially those present in low concentrations (below 1 vol. %). The response factors for the various gases (CO, $CO_2$, $C_3H_8$, $C_3H_6$, propylene oxide, and $C_2$ species) for both detectors were determined, for quantification purposes and to allow calculation of mass balances. The composition of product streams was also confirmed by mass spectroscopy, using a Dycor Quadlink spectrometer.

EXAMPLES 5–9

Catalyst Conversion and Selectivity

The following $Ag/Cl/NaNO_3/La/BaCO_3$ catalysts were prepared according to the methods described in Examples 1–3 and their activity assessed according to the method described in Example 4. The results presented in Table 2 were obtained after 2 hours of reaction time at 280° C.

TABLE 1

| Example | Transition Metal Promoter | Propane Conversion | Selectivity | | |
|---|---|---|---|---|---|
| | | | Propylene | Propylene Oxide | 1-Chloropropane |
| 5 | | 11% | 16% | 5% | 6% |
| 6 | 5% Cr* | 11% | 23% | 5% | 7% |
| 7 | 10% Cr* | 8% | 28% | 6% | 9% |
| 8 | Cu | 5% | 29% | 2% | 7% |
| 9 | Mg | 5° C. | 30% | 4% | 7% |

*Cr-content presented as percentage chromium hydroxy-carbonate

EXAMPLE 10

Activity Testing Using Increased Feed Ratio

The activities of all of the catalysts of Examples 1–3 were tested as described in Example 4, but a feedstream of 11% propane, 18% $O_2$, and balance He, at atmospheric pressure was used instead.

EXAMPLES 11–13

Catalyst Conversion and Selectivity

The following catalysts were prepared according to the methods described in Example 2 with 10% Cr as a percentage chromium hydroxy-carbonate and using Ba, Ca, and Sr supports. The activity of the catalysts was assessed according to the method described in Example 10. The results presented in Table 2 were obtained after 20 and 300 minutes of reaction time at 280° C.

TABLE 2

CATALYST ACTIVITY USING INCREASED FEED RATIO

| Example | Catalyst Support | Time (min) | Propane Conversion | Selectivity |  |  |
|---|---|---|---|---|---|---|
|  |  |  |  | Pro-pene | Propylene Oxide | 1-Chloropropane |
| 11 | $BaCO_3$ | 20 | 10% | 23% | 8% | 7% |
| 12 | $BaCO_3$ | 300 | 21% | 6% | 0.8% | 0.9% |
| 13 | $CaCO_3$ | 20 | 7.4% | 26% | 4% | 3% |
| 14 | $CaCO_3$ | 300 | 2.8% | 23% | 4% | 5% |
| 15 | $SrCO_3$ | 20 | 5.6% | 39% | 4% | 15% |
| 16 | $SrCO_3$ | 300 | 1.3% | 37% | 4% | 16% |

EXAMPLE 17

Precipitation Curve

The following precipitation curve (FIG. 1) was obtained using the method of Examples 1–3. The precipitation was conducted by injecting a solution containing 4 g/L NaOH and 60 g/L $K_2CO_3$ at 50 mL/h into a 250 mL solution of 5 g $Ca(NO_3)_2.4H_2O$ and 2.5 g $AgNO_3$, with vigorous stirring. The pH changes as a function of the amount of base solution injected and the amount of remaining $Ag^+$ and $Ca^+$ present in the solution. When the precipitation rate equals the rate of base(carbonate) injection, the pH attains a constant value.

We claim:

1. A process for the conversion of alkane to alkene comprising, contacting at a temperature in the range of approximately 200° C. to 400° C.:
   (a) a feedstream comprising alkane and an oxygen-containing gas; and
   (b) a supported silver catalyst comprising
      (i) an inert refractory solid support comprised of alkaline earth metal carbonate,
      (ii) a catalytically effective amount of silver,
      (iii) an effective promoting amount of a halide anion,
      (iv) an effective promoting amount of a rare earth metal promoter,
      (v) an effective promoting amount of a sodium promoter, and
      (vi) an optional effective promoting amount of a transition metal promoter.

2. A process of claim 1, wherein the catalyst is prepared by precipitation.

3. A process of claim 1, wherein the feedstream is essentially free of carbon dioxide.

4. The process of claim 1, wherein the rare earth metal promoter is lanthanum.

5. The process of claim 1, wherein the alkaline earth metal carbonate support is selected from the group consisting of strontium carbonate, calcium carbonate, barium carbonate and mixtures thereof.

6. The process of claim 5, wherein the alkaline earth metal carbonate is a barium carbonate support.

7. A process for the conversion of propane to propylene comprising contacting at a temperature in the range of approximately 250° C. to 350° C.:
   (a) a feedstream comprising propane and an oxygen-containing gas; and
   (b) a supported silver catalyst comprising
      (i) an inert refractory solid support comprised of alkaline earth metal carbonate,
      (ii) a catalytically effective amount of silver,
      (iii) an effective promoting amount of a halide anion,
      (iv) an effective promoting amount of a rare earth metal promoter,
      (v) an effective promoting amount of a sodium promoter, and
      (vi) an optional effective promoting amount of a transition metal promoter.

8. A process of claim 7, wherein the catalyst is prepared by precipitation.

9. A process of claim 7, wherein the feedstream is essentially free of carbon dioxide.

10. The process of claim 7, wherein the rare earth metal promoter is lanthanum.

11. The process of claim 7, wherein the alkaline earth metal carbonate support is selected from the group consisting of strontium carbonate, calcium carbonate, barium carbonate and mixtures thereof.

12. The process of claim 11, wherein the alkaline earth metal carbonate support is a barium carbonate support.

13. The process of claim 7, wherein the alkali metal halide is sodium chloride.

14. The process of claim 7, wherein the sodium promoter is sodium nitrate.

15. The process of claim 7, wherein the promoting amount of transition metal promoter is present.

16. The process of claim 15, wherein the transition metal promoter is selected from the group consisting of chromium, copper and magnesium.

17. The process of claim 16, wherein the transition metal promoter is chromium.

* * * * *